US009968140B2

(12) United States Patent
Rider et al.

(10) Patent No.: US 9,968,140 B2
(45) Date of Patent: May 15, 2018

(54) TECHNOLOGIES FOR MONITORING BREASTFEEDING

(71) Applicant: Intel Corporation, Santa Clara, CA (US)

(72) Inventors: Tomer Rider, Naahryia (IL); Shahar Taite, Kfar Saba (IL); Aviv Ron, Nir Moshe (IL)

(73) Assignee: Intel Corporation, Santa Clara, CA (US)

( * ) Notice: Subject to any disclaimer, the term of this patent is extended or adjusted under 35 U.S.C. 154(b) by 577 days.

(21) Appl. No.: 14/583,670

(22) Filed: Dec. 27, 2014

(65) Prior Publication Data
US 2016/0183602 A1 Jun. 30, 2016

(51) Int. Cl.
*A41C 3/04* (2006.01)
*A61B 5/00* (2006.01)
(Continued)

(52) U.S. Cl.
CPC .............. *A41C 3/04* (2013.01); *A41C 3/005* (2013.01); *A61B 5/4288* (2013.01);
(Continued)

(58) Field of Classification Search
CPC .......... A41D 1/205; A41C 3/04; A41C 3/005; A41C 3/02; A61M 1/06; A44B 11/00–11/28; A44B 13/00; A44B 13/01; A44B 13/02; A44B 17/00; A44B 18/00; A44B 99/00; A44B 99/005
(Continued)

(56) References Cited

U.S. PATENT DOCUMENTS 6,109,100 A * 8/2000 Buckley .................... A61J 9/00
604/76
2008/0287770 A1* 11/2008 Kurzweil ............. A61B 5/0408
600/388
(Continued)

FOREIGN PATENT DOCUMENTS

| WO | 2014-087343 | | 6/2014 |
| WO | WO 2014/087343 | * | 6/2014 |
| WO | WO 2015/121773 | * | 8/2015 |

OTHER PUBLICATIONS

International Search Report for PCT/US15/061612, dated Feb. 29, 2016 (3 pages).

(Continued)

*Primary Examiner* — Mohamed Charioui
*Assistant Examiner* — Catherine Rastovski
(74) *Attorney, Agent, or Firm* — Barnes & Thornburg LLP

(57) ABSTRACT

Technologies for monitoring breastfeeding include a smart breast support garment computing system of a breast support garment. The smart breast support garment computing system includes a use sensor and a latch sensor. Further, the smart breast support garment computing system is to determine whether the breast support garment is in use based on the sensor data generated by the use sensor and a state of a breast latch of the breast support garment based on sensor data generated by the latch sensor. The smart breast support garment computing system further records one or more breastfeeding events in response to a determination that the breast support garment is in use and the breast latch is open.

20 Claims, 8 Drawing Sheets

(51) Int. Cl.
*A61M 1/06* (2006.01)
*A41C 3/00* (2006.01)
*G06F 19/00* (2018.01)

(52) U.S. Cl.
CPC ............ *A61B 5/6804* (2013.01); *A61M 1/06* (2013.01); *A61M 2205/3553* (2013.01); *A61M 2205/3584* (2013.01); *A61M 2205/50* (2013.01); *G06F 19/3406* (2013.01)

(58) Field of Classification Search
USPC ............... 2/104; 450/36, 37, 38; 604/75–79, 604/345–346
See application file for complete search history.

(56) References Cited

U.S. PATENT DOCUMENTS

| | | | | |
|---|---|---|---|---|
| 2009/0054771 A1* | 2/2009 | Kolberg | ............... | A61B 5/4288 600/438 |
| 2012/0188778 A1* | 7/2012 | Buettner | ............ | A44B 11/2565 362/487 |
| 2012/0277636 A1* | 11/2012 | Blondheim | .............. | A61B 5/11 600/595 |
| 2012/0284251 A1* | 11/2012 | Haas | ................. | G06F 17/30864 707/709 |
| 2015/0094830 A1* | 4/2015 | Lipoma | ................. | G05B 15/02 700/90 |

OTHER PUBLICATIONS

Written Opinion for PCT/US15/061612, dated Feb. 29, 2016 (6 pages).

* cited by examiner

TECHNOLOGIES FOR MONITORING BREASTFEEDING

BACKGROUND

Breastfeeding or nursing mothers often record the number of times and the duration of breastfeeding so that they can monitor the status and amount of feeding. Such monitoring may even be critical in the first month of the baby's life to track the feeding habits and health of the baby. Mothers generally resort to manually recording the feeding times and amounts on a notepad or digitally (e.g., via an application). However, in doing so, breastfeeding mothers often forget to note the breastfeeding occurrences and are therefore unable to accurately track whether the baby is eating enough. As such, it may be difficult for the mother to provide sufficient information to a medical professional to allow the professional to properly address any potential baby nutrition concerns.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
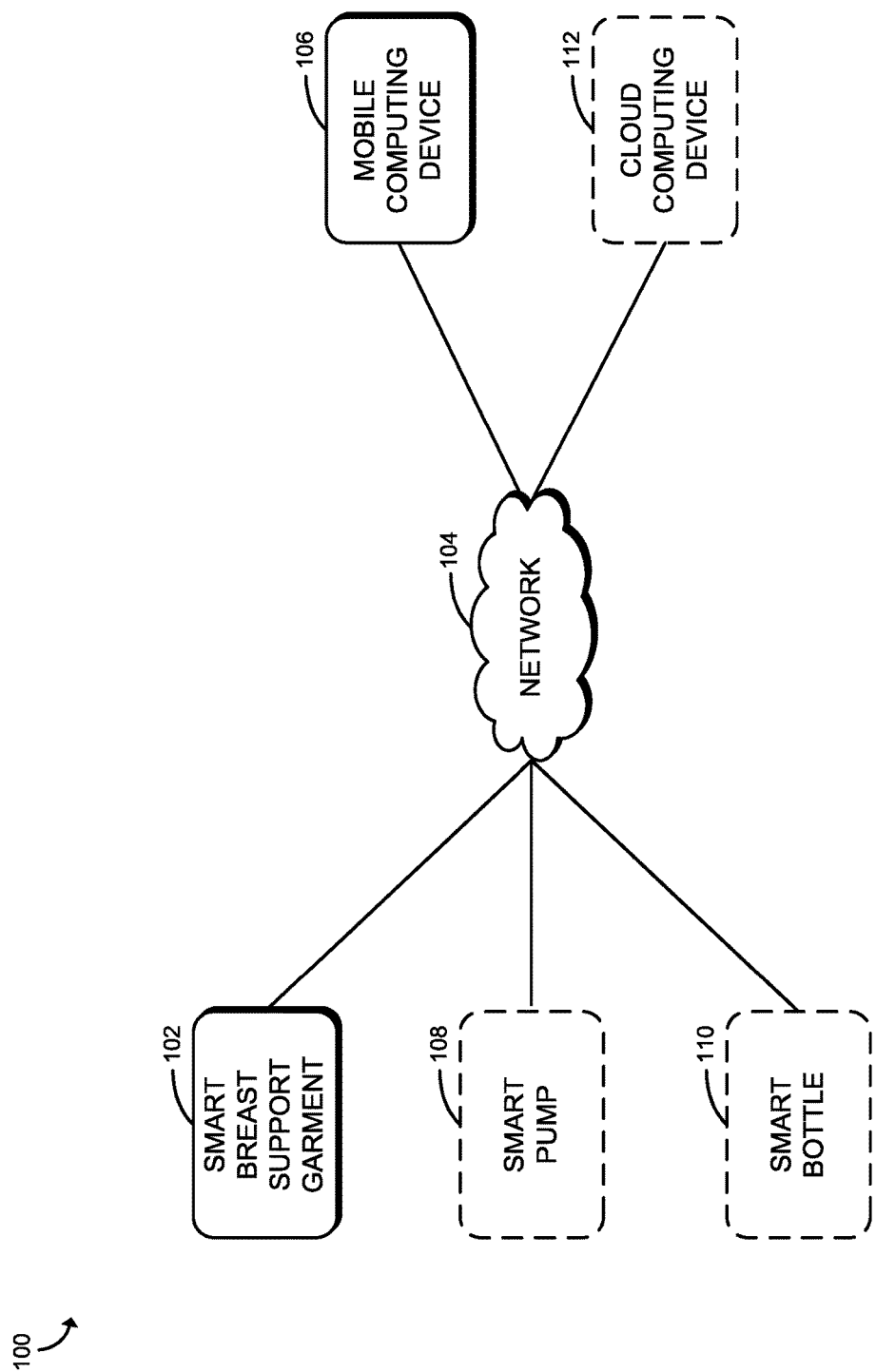
FIG. 1 is a simplified block diagram of at least one embodiment of a system for monitoring breastfeeding.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C): (A and B); (B and C); (A and C); or (A, B, and C). Similarly, items listed in the form of "at least one of A, B, or C" can mean (A); (B); (C): (A and B); (B and C); (A and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a system 100 for monitoring breastfeeding illustratively includes a smart breast support garment 102, a network 104, and a mobile computing device 106. Additionally, in some embodiments, the system 100 may include a smart pump 108, a smart bottle 110, and/or a cloud computing device 112. Although only one smart breast support garment 102, one network 104, one mobile computing device 106, one smart pump 108, one smart bottle 110, and one cloud computing device 112 are illustratively shown in FIG. 1, the system 100 may include any number of smart breast support garments 102, networks 104, mobile computing devices 106, smart pumps 108, smart bottles 110, and/or cloud computing devices 112 in other embodiments. For example, in some embodiments, the smart breast support garment 102 may communicate with the mobile computing device 106 over one network 104 (e.g., over a P2P connection via Bluetooth®), and the mobile computing device 106 may communicate with the cloud computing device 112 (e.g., in a cloud computing environment) over a different network 104. In another embodiment, the smart breast support garment 102 may, for example, be utilized in conjunction with multiple smart bottles 110.

As described in detail below, the smart breast support garment 102 is configured to log various events associated with breastfeeding (e.g., the time and duration of each breastfeeding session). In particular, the smart breast support garment 102 or, more particularly, a computing system of the smart breast support garment 102 may determine whether the smart breast support garment 102 is in use and also determine a state of a breast latch of the smart breast support garment 102 based on sensor data generated by one or more sensors embedded within or otherwise secured to the smart breast support garment 102. In some embodiments, the smart breast support garment 102 records breastfeeding events in response to determining that the smart breast support garment 102 is in use and the breast latch is open. The breastfeeding events may include any events associated with the breastfeeding of an infant or related activity (e.g., using a breast pump) based on the generated data. For example, the smart breast support garment 102 may record the time and duration of breastfeeding associated with the period of time between the breast latch of the smart breast support garment 102 (e.g., a nursing bra) being opened and the breast latch being closed. It should be appreciated that the smart breast support garment 102 is "smart" in the sense that it includes a computing system (e.g., integrally formed with or otherwise secured to the corresponding breast support garment) and/or one or more sensors.

In the illustrative embodiment, the mobile computing device 106 receives various breastfeeding event data from the smart breast support garment 102 and analyzes the data to determine, for example, a feeding routine of an infant. As described below, in some embodiments, the mobile computing device 102 may receive the breastfeeding event data from the smart breast support garment 102 over the network 104, whereas in other embodiments, the breastfeeding event data may be retrieved from a memory device (e.g. a removable memory device) of the smart breast support garment 102. Additionally, in some embodiments, the mobile computing device 102 may retrieve additional recorded data from a smart pump 108 and/or a smart bottle 110 (e.g., to provide a more holistic analysis of infant feeding habits). It should be appreciated that the breastfeeding events may be analyzed for any number of reasons. For example, a pediatrician may access the breastfeeding event data, or an analyzed version thereof, to determine the feeding habits of the infant and more adequately assess the health of the baby. In other embodiments, the mobile computing device 102 or the cloud computing device 112 may provide the user with suggestions and/or reminders (e.g., the next breastfeeding time) based on, for example, the sensor data, breastfeeding event data, and/or data learned from analyses of the data (e.g., historical data/patterns).

Figure 2:
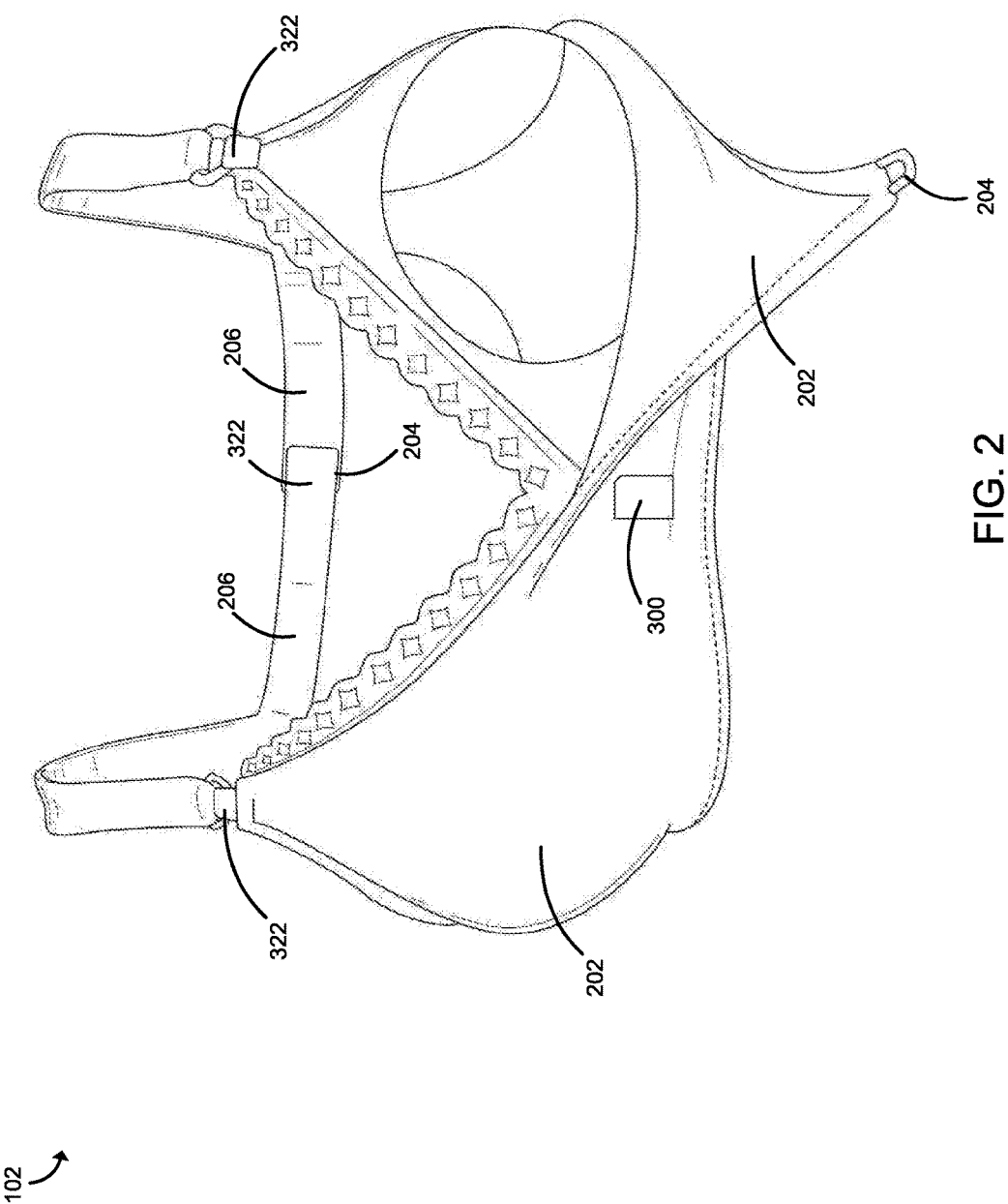
FIG. 2 is a simplified diagram of at least one embodiment of a smart breast support garment of the system of FIG. 1.

Referring now to FIG. 2, an illustrative embodiment of the smart breast support garment 102 is shown. In the illustrative embodiment, the smart breast support garment 102 is depicted as a brassiere or bra that permits a mother to breastfeed/nurse an infant without removing the garment 102. However, it should be appreciated that the garment 102 may be otherwise embodied. For example, in some embodiments, the garment 102 may be embodied as a shirt that includes the features described herein and/or is otherwise capable of performing the functions described herein. The illustrative garment 102 includes at least one breast cover 202 that may be opened and closed to permit selective breastfeeding/nursing without removing the garment 102. That is, a mother may wear the garment 102 with the breast cover 202 closed or secured throughout the day and, when it is necessary to breastfeed an infant (or pump breast milk), the breast cover 202 may be opened or unsecured to permit such breastfeeding. In the illustrative embodiment of FIG. 2, it should be appreciated that the left breast cover 202 is shown in an open configuration and the right breast cover 202 is shown in the closed configuration.

Figure 3:
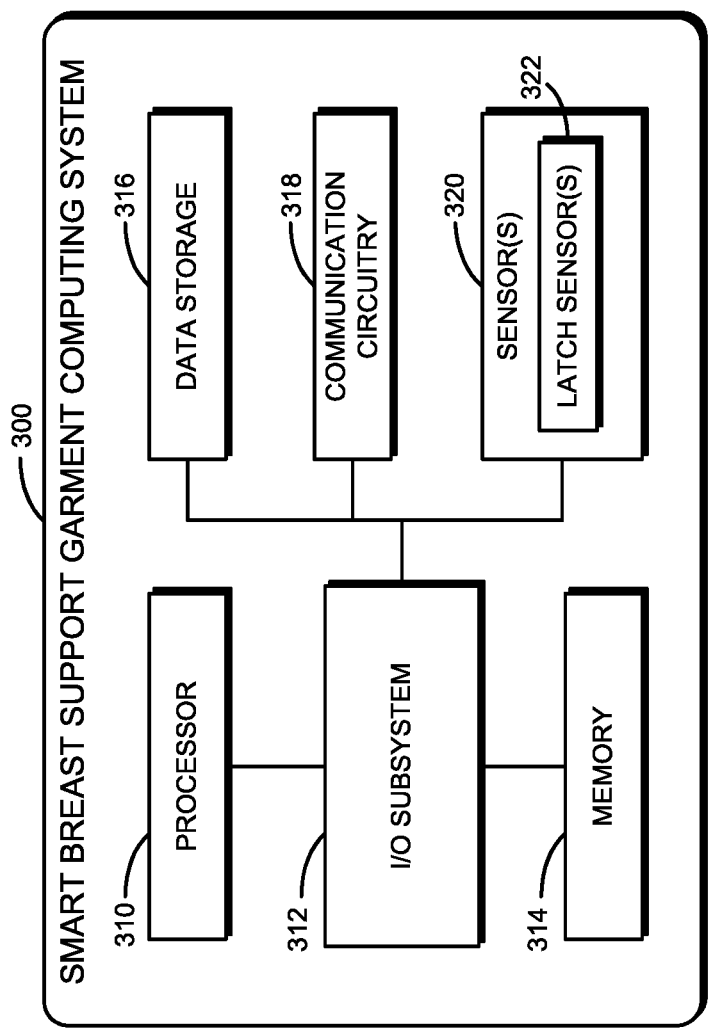
FIG. 3 is a simplified block diagram of at least one embodiment of a smart breast support garment computing system of the smart breast support garment of FIG. 2.

The illustrative smart breast support garment 102 includes a smart breast support garment computing system 300 as shown in FIG. 3. Referring now to FIG. 3, the illustrative breast support garment computing system 300 includes a processor 310, an input/output ("I/O") subsystem 312, a memory 314, a data storage 316, a communication circuitry 318, and one or more sensors 320. Of course, the breast support garment computing system 300 may include other or additional components, such as those commonly found in a typical computing device (e.g., various input/output devices and/or other components), in other embodiments. Additionally, in some embodiments, one or more of the illustrative components may be incorporated in, or otherwise form a portion of, another component. For example, the memory 314, or portions thereof, may be incorporated in the processor 310 in some embodiments. In the illustrative embodiment, the smart breast support garment computing system 300 is integrated with the garment 102. In other embodiments, the computing system 300 may be embodied as a conversion kit such that the computing system 300 may be secured to, for example, a traditional breast support garment (e.g., an ordinary nursing bra).

The processor 310 may be embodied as any type of processor capable of performing the functions described herein. For example, the processor 310 may be embodied as a single or multi-core processor(s), digital signal processor, microcontroller, or other processor or processing/controlling circuit. It should be appreciated that the memory 314 may be embodied as any type of volatile or non-volatile memory or data storage capable of performing the functions described herein. In operation, the memory 314 may store various data and software used during operation of the computing system 300 such as operating systems, applications, programs, libraries, and drivers. The memory 314 is communicatively coupled to the processor 310 via the I/O subsystem 312, which may be embodied as circuitry and/or components to facilitate input/output operations with the processor 310, the memory 314, and other components of the breast support garment computing system 300. For example, the I/O subsystem 312 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 312 may form a portion of a system-on-a-chip (SoC) and be incorporated, along with the processor 310, the memory 314, and other components of the breast support garment computing system 300, on a single integrated circuit chip.

The data storage 316 may be embodied as any type of device or devices configured for short-term or long-term storage of data such as, for example, memory devices and circuits, memory cards, hard disk drives, solid-state drives, or other data storage devices. For example, as described below, the data storage 316 may include a flash drive, secure digital (SD) card, and/or another data storage device configured to store breastfeeding data, breastfeeding events, and/or other data. The data storage 316 and/or the memory 314 may store various data during operation of the breast support garment computing system 300 useful for performing the functions described herein.

The communication circuitry 318 may be embodied as any communication circuit, device, or collection thereof, capable of enabling communications between the breast support garment computing system 300 and other remote devices over the network 104 (e.g., the mobile computing device 106). The communication circuitry 318 may be configured to use any one or more communication technologies (e.g., wireless or wired communications) and associated protocols (e.g., Ethernet, Bluetooth®, Wi-Fi®, WiMAX, etc.) to effect such communication.

The sensors 320 generate sensor data regarding a user of the breast support garment 102, the environment of the breast support garment 102, the breast support garment 102 itself, and/or other data useable by the computing system 300 in determining the occurrence of various breastfeeding events as described herein. As shown, the sensors 320 illustratively include one or more latch sensors 322. As described below, the latch sensors 322 are configured to generate sensor data indicative of a state of one or more latches 204 of the breast support garment 102 (e.g., whether the latch is opened/unsecured or closed/secured). For example, as shown in the illustrative embodiment of FIG. 2, the breast cover 202 may be opened and closed for breastfeeding by virtue of the corresponding latch 204. In the illustrative embodiment, the latch sensors 322 may be positioned and configured to detect the state of the breast latch 204 (e.g., open/closed), the relative position of the breast latch 204 to the latch sensors 322, and/or other data associated with the breast covers 202 and/or latches 204. As described below, such data may be analyzed to determine, for example, a time and duration for which an infant is breastfed. It should be appreciated that each of the latches 204 described herein may be embodied as one or more hooks, snaps, loops, Velcro strips, ties, magnets, self-releasing adhesive strips, buttons, and/or any other suitable fasteners.

Similarly, in some embodiments, the breast support garment 102 may include back straps 206 that are connected to one another (e.g., via latches 204) to secure the breast support garment 102 to the wearer (the breastfeeding mother). In such embodiments, one or more latch sensors 322 may be positioned (e.g., on the back straps 206) to determine whether the back straps 206 are secured to one another. As described below, the computing system 300 may utilize such sensed data to determine, for example, whether the breast support garment 102 is in use. For example, in some embodiments, the computing system 300 may assume that the breast support garment 102 is only in use when the back straps 206 are secured to one another (e.g., via the latches 204) and record (or not record) sensor data generated by the other sensors 320 accordingly. Of course, as described below, the breast support garment 102 may include additional or alternative latches and/or straps configured to secure the breast support garment 102 to the wearer (e.g., a front-latching nursing bra or a strapless nursing bra). In such embodiments, the computing system 300 may record/analyze sensor data from corresponding latches or otherwise determine when the breast support garment 102 is in use.

Additionally, in some embodiments, the sensors 320 may include one or more other sensors to perform various functions. For example, in some embodiments, the sensors 320 may include a pressure sensor, proximity sensor, skin sensor (e.g., a galvanic skin response (GSR) sensor), and/or another suitable sensor to determine whether the breast support garment 102 is in use. Additionally or alternatively, the sensors 320 may include a pressure sensor positioned on the breast cover 202 and configured to determine the pressure of the corresponding breast of the mother and thereby estimate an amount of breast milk accumulated in the breast (e.g., to calculate the next appropriate breastfeeding time). Further, in some embodiments, the sensors 320 may include an audio sensor to detect sounds in the environment, which may be used by the computing system 300, for example, to differentiate data collected during the breastfeeding of an infant and data collected during the use of a breast pump. It should be appreciated that, in some embodiments, the sensors 320 may be embodied as, or otherwise include, other sensors to sense data useful in analyzing the breastfeeding patterns of a mother to an infant. In various embodiments, the sensors 320 may be embodied as, or otherwise include, for example, proximity sensors, optical sensors, light sensors, audio sensors, temperature sensors, motion sensors, piezoelectric sensors, cameras, and/or other types of sensors. Of course, the computing system 300 may also include components and/or devices configured to facilitate the use of the sensor(s) 320. It should further be appreciated that the sensors 320 and/or latches 204 may vary depending on the particular embodiment.

Referring back to FIG. 1, the network 104 may be embodied as any type of communication network capable of facilitating communication between the smart breast support garment computing system 300 and remote devices (e.g., the mobile computing device 106). As such, the network 104 may include one or more networks, routers, switches, computers, and/or other intervening devices. For example, the network 104 may be embodied as or otherwise include one or more cellular networks, telephone networks, local or wide area networks, publicly available global networks (e.g., the Internet), an ad hoc network, or any combination thereof.

The mobile computing device 106 and/or the cloud computing device 112 may be embodied as any computing device capable of performing the functions described herein. For example, the mobile computing device 106 and/or the cloud computing device 112 may be embodied as a cellular phone, smartphone, wearable computing device, personal digital assistant, mobile Internet device, laptop computer, tablet computer, notebook, netbook, Ultrabook™, desktop computer, server, router, switch, Hybrid device, and/or any other computing/communication device. In some embodiments, the mobile computing device 106 and/or the cloud computing device 112 may include components similar to the components of the computing system 300 described above and/or components commonly found in a computing device such as a processor, memory, I/O subsystem, data storage, peripheral devices, and so forth, which are not illustrated in FIG. 1 for clarity of the description. Further, in some embodiments, the cloud computing device 112 forms a portion of a cloud computing environment or system.

The smart pump 108 may be embodied as any breast pump that is configured to sense data associated with breastfeeding or related events. As such, the smart pump 108 may include a computing system and/or include components similar to the computing system 300 described above. For example, in some embodiments, the smart pump 108 may establish a communication pairing with the smart breast support garment 102 or the mobile computing device 106 (e.g., via a near-field communication (NFC) tap). By doing so, the smart breast support garment 102, the smart pump 108, and/or the mobile computing device 106 may determine, for example, whether breastfeeding events (e.g., latch openings) should be associated with breastfeeding an infant or breast pumping with the smart pump 108.

The smart bottle 110 may be embodied as any infant-feeding bottle that is configured to sense data associated with feeding an infant. As such, the smart bottle 110 may include a computing system and/or include components similar to the computing system 300 described above. For example, in some embodiments, the smart bottle 110 may establish a communication pairing with the smart breast support garment 102 or the mobile computing device 106 (e.g., via an NFC tap). In some embodiments, the smart bottle 110 includes one or more sensors configured to measure or otherwise determine the amount of fluid (e.g., breast milk) entering and/or leaving the bottle 110. For example, the smart bottle 110 may determine the amount of breast milk (e.g., the number of ounces) pumped into the bottle 110 by the smart pump 108 or another suitable pump (e.g., a traditional breast pump) and/or the amount of breast milk expressed from the bottle 110 (e.g., during breastfeeding).

It should be appreciated that data sensed by the smart bottle 110 may be utilized to determine feeding times of an infant and, in conjunction with the other components of the system 100, determine an entire feeding schedule of an infant. For example, in some embodiments, the system 100 may be utilized to determine breastfeeding times, breast pumping times, and/or bottle-feeding times (e.g., including the amount of milk delivered), which the mobile computing device 106 and/or the cloud computing device 112 may utilize for various analytics. In some embodiments, the system 100 may include other smart nursing/feeding accessories that collect data useful in determining breastfeeding or infant feeding patterns and related information.

Figure 4:
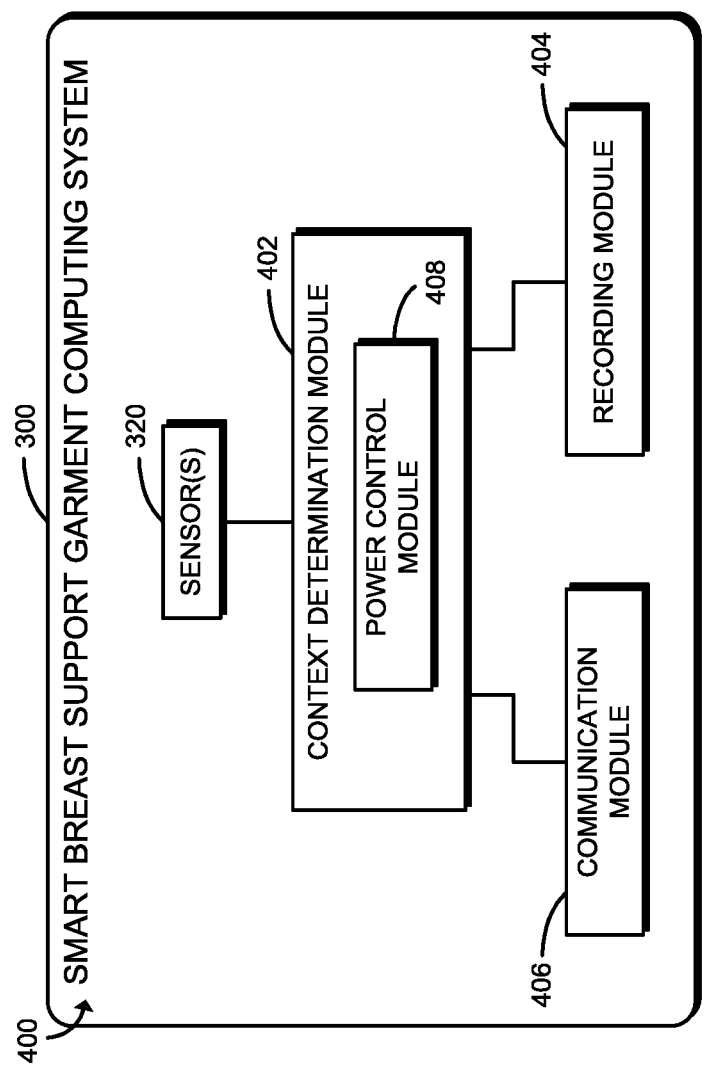
FIG. 4 is a simplified block diagram of at least one embodiment of an environment of the smart breast support garment computing system of FIG. 3.

Referring now to FIG. 4, in use, the smart breast support garment computing system 300 establishes an environment 400 for monitoring breastfeeding. The illustrative environment 400 includes a context determination module 402, a recording module 404, and a communication module 406. Additionally, the context determination module 402 includes a power control module 408. The various modules of the environment 400 may be embodied as hardware, software, firmware, or a combination thereof. For example, the various modules, logic, and other components of the environment 400 may form a portion of, or otherwise be established by, the processor 310 or other hardware components of the computing system 300. As such, in some embodiments, one or more of the modules of the environment 400 may be embodied as a circuit or collection of electrical devices (e.g., a context determination circuit, a recording circuit, and/or a communication circuit). Additionally, in some embodiments, one or more of the illustrative modules may form a portion of another module and/or one or more of the illustrative modules may be embodied as a standalone or independent module.

The context determination module 402 is configured to process and/or analyze data generated by the sensors 320. As described herein, in some embodiments, the context determination module 402 may determine various information (e.g., breastfeeding events) based on the state of one or more latches 204 (e.g., open/closed) based on the latch sensor(s) 322. For example, the context determination module 402 may determine whether the breast support garment 102 is in use based on the state of a back latch 204 of the breast support garment 102. Further, in the illustrative embodiment, the context determination module 402 may determine whether a breast latch 204 is open for breastfeeding and/or breast pumping. Of course, the context determination module 402 may determine other contextual information associated with breastfeeding as well.

As indicated above, in the illustrative embodiment, the context determination module 402 includes the power control module 408; however, it should be appreciated that the power control module 408 may be embodied as a standalone or independent module in other embodiments. The power control module 408 is configured to provide power to one or more components of the smart breast support garment computing system 300. For example, in some embodiments, the power control module 408 may provide power to one or more components of the smart breast support garment computing system 300 in response to a determination that the breast latch is open. In doing so, the power control module 408 may, for example, permit the smart breast support garment computing system 300 to conserve power when the breast support garment 102 is not being used to breastfeed and/or pump breast milk (e.g., by maintaining the computing system 300 in a low-power or standby state).

The recording module 404 is configured to record generated sensor data, breastfeeding events, and/or related data to the memory 314 and/or data storage 316 of the computing system 300. In some embodiments, the recording module 404 records the corresponding data to a microSD card, a flash drive, and/or another removable memory device. For example, in some embodiments, the removable memory device may be removed from the computing system 300 and read by the mobile computing device 106. In other embodiments, the mobile computing device 106 may retrieve the data stored by the recording module 404 and/or analyzed versions thereof from the computing system 300 over a communication pairing between the devices. In yet other embodiments, the recording module 404 may record the generated sensor data, breastfeeding event, and/or related data directly to the mobile computing device 106. As described below, in some embodiments, the recording module 404 may record the point in time at which a latch 204 changes states (e.g., is opened or closed), the duration a latch 204 is maintained in a state, and/or other suitable information. In some embodiments, the recording module 404 only records data when the breast support garment 102 is determined to be in use.

The communication module 406 handles the communication between the computing system 300 and remote devices (e.g., the mobile computing device 106) through the network 104. For example, as described herein, the communication module 406 may transmit the recorded sensor data, the breastfeeding event data, and/or other data to the mobile computing device 106 and/or other remote computing devices.

Figure 5:
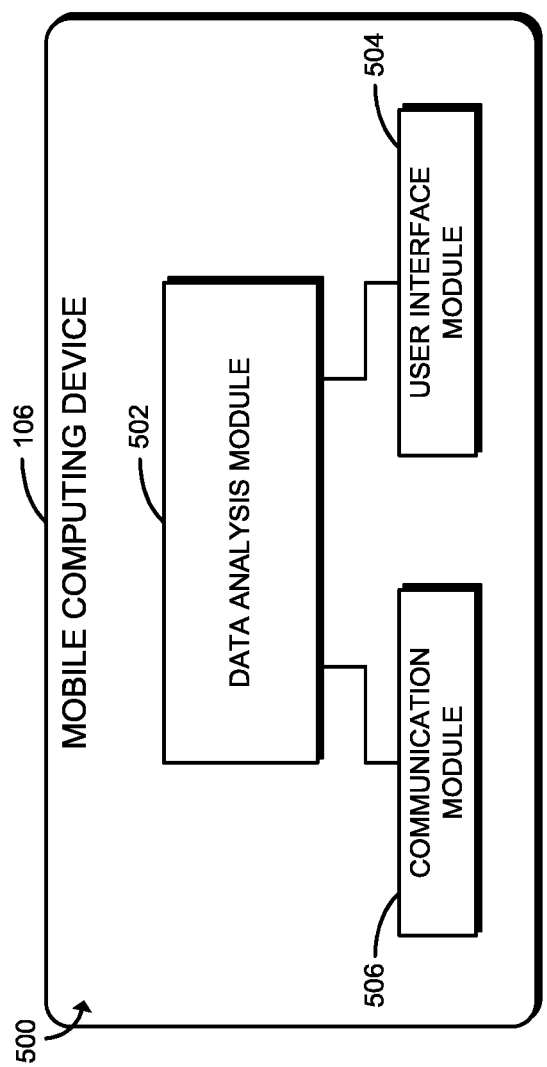
FIG. 5 is a simplified block diagram of at least one embodiment of an environment of a mobile computing device of the system of FIG. 1.

Referring now to FIG. 5, in use, the mobile computing device 106 establishes an environment 500 for analyzing breastfeeding data. The illustrative environment 500 includes a data analysis module 502, a user interface module 504, and a communication module 506. The various modules of the environment 500 may be embodied as hardware, software, firmware, or a combination thereof. For example, the various modules, logic, and other components of the environment 500 may form a portion of, or otherwise be established by, the processor or other hardware components of the mobile computing device 106. As such, in some embodiments, one or more of the modules of the environment 500 may be embodied as a circuit or collection of electrical devices (e.g., a data analysis circuit, a user interface circuit, and/or a communication circuit). Additionally, in some embodiments, one or more of the illustrative modules may form a portion of another module.

The data analysis module 502 is configured to analyze the breastfeeding event data, sensor data, and/or other data received from the computing system 300 of the breast support garment 102 or the removable memory device of the computing system 300. For example, the data analysis module 502 may determine a feeding routine/pattern of an infant based on the breastfeeding events logged by the computing system 300. As discussed above, in some embodiments, the system 100 includes a smart pump 108 and/or a smart bottle 110. In such embodiments, the data analysis module 502 may also utilize the data recorded by those devices in determining the feeding routine/pattern of the infant. The data analysis module 502 may determine, for example, the time and duration of breastfeeding occurrences. In other embodiments, the data analysis module 502 analyzes the sensor data generated by the sensors 320 of the smart breast support garment 102 to determine the occurrence of various breastfeeding events and determine the feeding routine/pattern of the infant.

The user interface module 504 permits a user of the mobile computing device 106 to interact with the mobile computing device 106. For example, in some embodiments, the user interface module 504 permits a user to view statistics and/or other representations of the number of breast feedings, the side of the breast that breast feedings occurred, the duration of breast feedings, the time between breast feedings, and/or other useful data associated with infant feeding. Further, in some embodiments, the user interface module 504 may suggest the next feeding time to the mother (e.g., based on a historical breastfeeding pattern and/or sensed breast pressure). For example, in some embodiments, the computing system 300 may include one or more sensors 320 that generate sensor data indicative of a breast pressure of a wearer of the breast support garment 102 (e.g., indicative of an amount of breast milk stored by the corresponding breast of the wearer), which may be utilized to determine appropriate breastfeeding and/or breast pumping times. In some embodiments, the user interface module 504 enables the user to edit (e.g., add, delete, and/or modify) the recorded data manually. For example, the mother may enter data associated with a breastfeeding done with a different breast support garment or without a breast support garment.

The communication module 506 handles the communication between the mobile computing device 106 and remote devices (e.g., the breast support garment 102) through the network 104. For example, in some embodiments, the communication module 506 may establish a communication pairing with the breast support garment 102 to receive breastfeeding event data.

Figure 6:
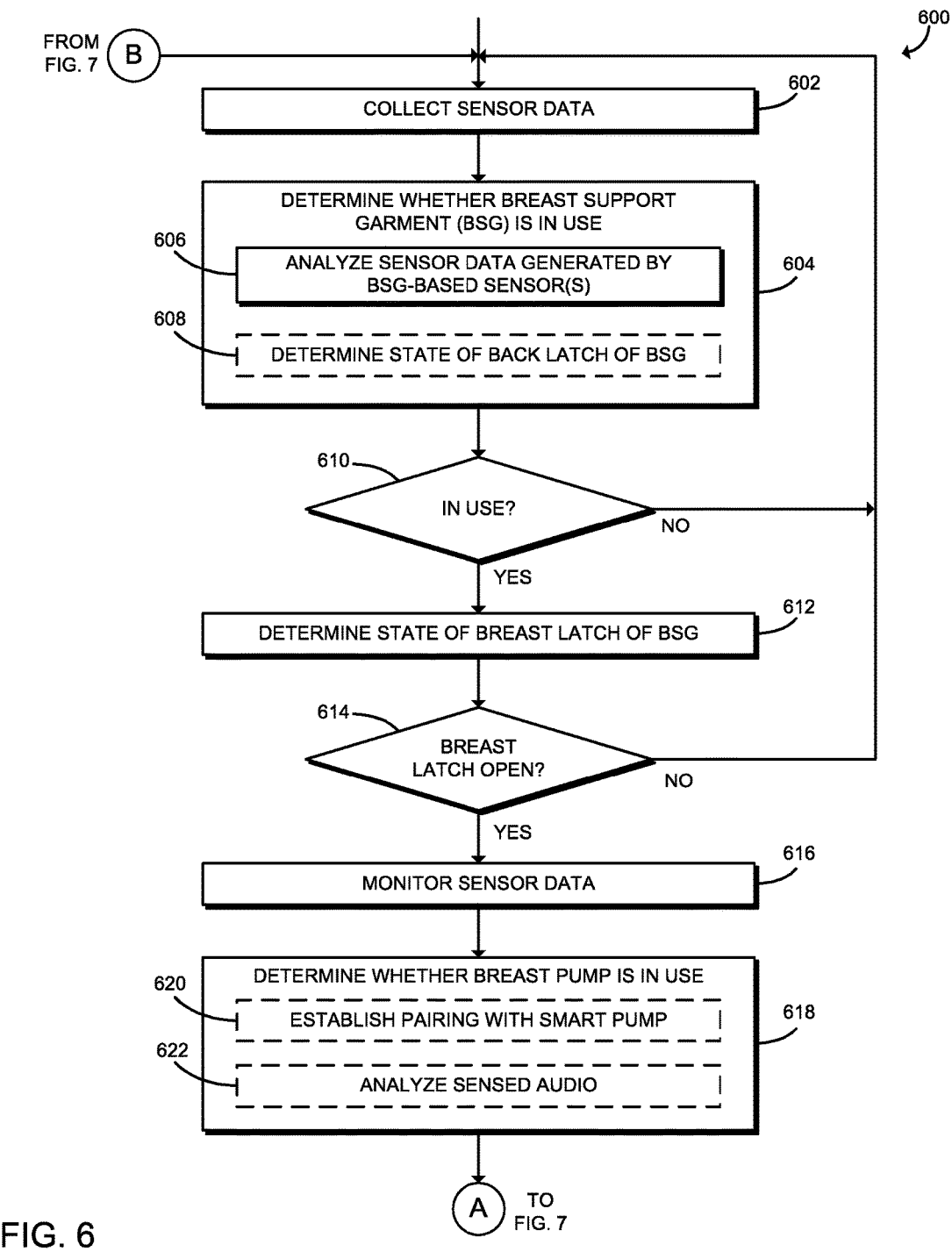
FIGS. 6-7 is a simplified flow diagram of at least one embodiment of a method for monitoring breastfeeding that may be executed by the smart breast support garment computing system of FIG. 3.
Figure 7:
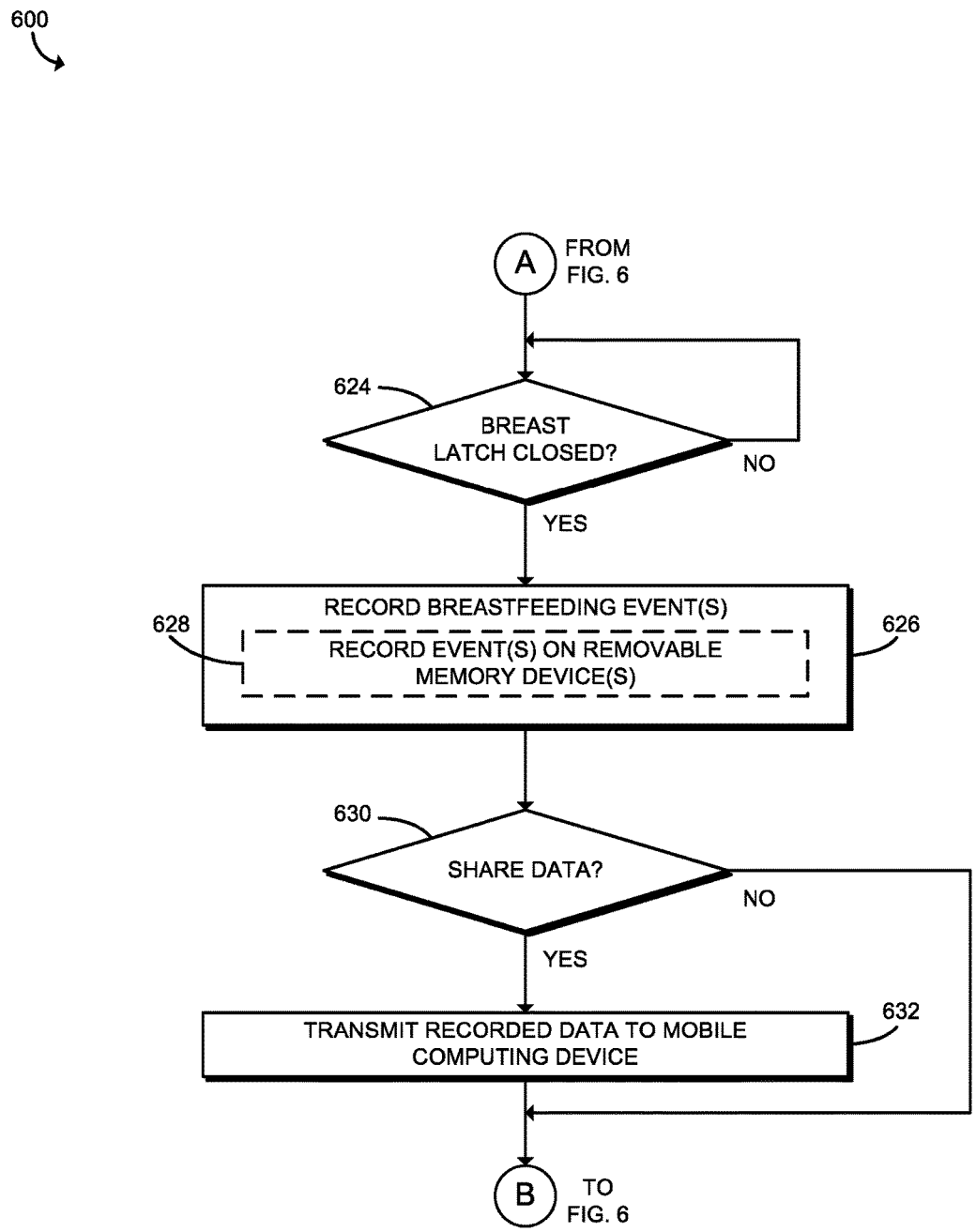

Referring now to FIGS. 6-7, in use, the breast support garment computing system 300 may execute a method 600 for monitoring breastfeeding. The illustrative method 600 begins with block 602 in which the breast support garment computing system 300 collects the sensor data generated by the sensors 320 of the breast support garment computing system 300. In block 604, the computing system 300 whether the breast support garment 102 is in use (i.e., being worn by the mother). In doing so, in block 606, the computing system 300 may analyze the sensor data generated by the sensors 320. For example, in block 608, the computing system 300 may determine a state of the back latch 204 of the breast support garment 102 and conclude that the breast support garment 102 is in use if the back latch 204 is closed. Of course, in some embodiments, the particular breast support garment 102 may be, additionally or alternatively, secured at the front (e.g., via a front latch 204) and/or another location in which case the computing system 300 may determine the state of the corresponding garment securing latch(es) 204. In other embodiments, the breast support garment 102 may have no such latch 204 to secure it to the wearer (e.g., a compression garment, strapless bra, or "sports" bra) in which case the computing system 300 may otherwise determine whether the garment 102 is being worn. For example, in another embodiment, the computing system 300 may utilize a skin sensor (e.g., a GSR), proximity sensor, pressure sensor, and/or temperature sensor to determine whether the breast support garment 102 is being worn at a particular point in time.

If the computing system 300 determines, in block 610, that the breast support garment 102 is in use, the computing system 300 determines the state of a breast latch 204 of the breast support garment 102 (i.e., whether the breast latch 204 is open or closed). As discussed above, in the illustrative embodiment, the breast latch 204 secures the breast cover 202. If the computing system 300 determines, in block 614, that the breast latch 204 is open, the computing system 300 monitors sensor data generated by the sensors 320 in block 616. In other words, in some embodiments, the computing system 300 determines to analyze the sensor data for various breastfeeding events when the breast support garment 102 is determined to be in use and the breast latch 204 is open. In some embodiments, the computing system 300 may operate in a low-power state when either of those conditions is not met. However, in other embodiments, the computing system 300 may continuously monitor/analyze sensor data for breastfeeding events.

In block 618, the computing system 300 determines whether a breast pump is in use (e.g., in conjunction with the garment 102). In doing so, in block 620, the computing system 300 may establish a communication pairing with the breast pump if the breast pump is a smart pump 108 (e.g., if the breast pump includes a computing system). In some embodiments, the computing system 300 may distinguish breastfeeding from breast pumping based on whether there exists a communication pairing between the computing system 300 and the smart pump 108. Alternatively or additionally, in block 622, the computing system 300 may analyze audio data generated by one or more audio sensors 320 of the computing system 300. For example, the computing system 300 may differentiate between breastfeeding and breast pumping based on the corresponding audio profiles associated with each of those activities. As described herein, breastfeeding and breast pumping may be distinguished in order to generate a more accurate representation of the feeding pattern of the infant.

In block 624 of FIG. 7, the computing system 300 determines whether the breast latch 204 is closed. If so, the computing system 300 records one or more breastfeeding events in block 626. For example, the computing system 300 may record the time and duration of the breastfeeding that occurred between a point in time at which the breast latch 204 was opened and a point in time at which the breast latch 204 was closed. Of course, the computing system 300 may record various other breastfeeding events (e.g., the breast used for breastfeeding, whether breastfeeding or pumping occurred, etc.). As described above, in some embodiments, the computing system 300 may record the breastfeeding events on one or more removable memory devices in block 628.

In block 630, the computing system 300 determines whether to share the recorded data. If so, the computing system 300 transmits the recorded data to the mobile computing device 106 in block 632. In some embodiments, the recorded breastfeeding events, sensed data, and/or other information may be transmitted to the mobile computing device 106 in response to a request from the mobile computing device 106 (e.g., user input). In other embodiments, the computing system 300 may transmit the recorded data to the mobile computing device 106 on its own initiative or in response to some other condition (e.g., periodically). Further, as discussed above, the mobile computing device 106 may read the recorded data from a removable memory device in some embodiments.

Figure 8:
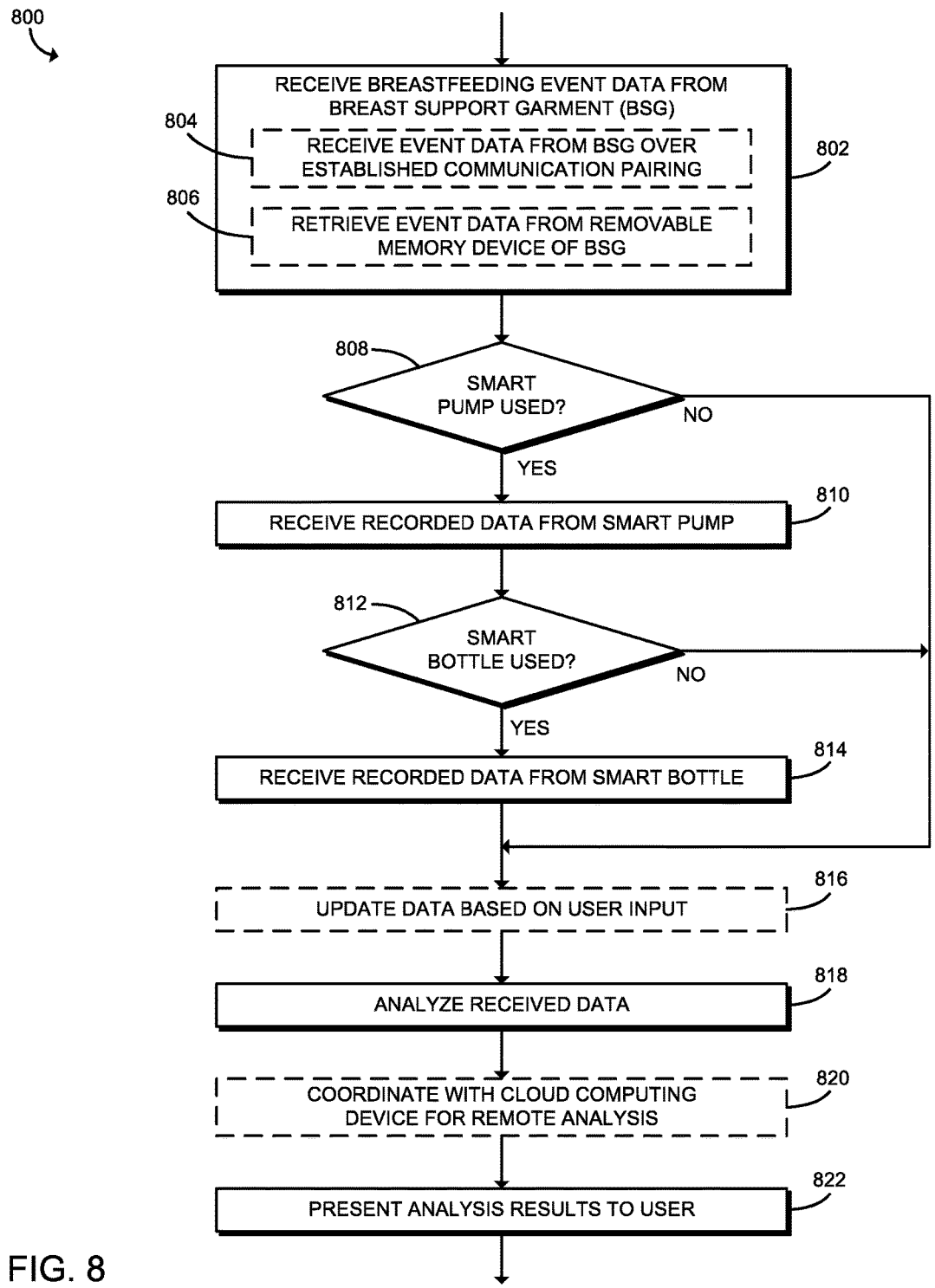
FIG. 8 is a simplified flow diagram of at least one embodiment of a method for analyzing breastfeeding data that may be executed by the mobile computing device of the system of FIG. 1.

Referring now to FIG. 8, in use, the mobile computing device 106 may execute a method 800 for analyzing breastfeeding data. The illustrative method 800 begins with block 802 in which the mobile computing device 106 receives breastfeeding event data from the breast support garment 102. As described above, the mobile computing device 106 may access such breastfeeding data in a variety of ways. For example, in block 804, the mobile computing device 106 may receive the breastfeeding event data from the breast support garment 102 or, more particularly, the breast support garment computing system 300 over an established communication pairing (e.g., an NFC tap, Bluetooth™, etc.) between the mobile computing device 106 and the computing system 300. In another embodiment, in block 806, the mobile computing device 106 may retrieve the breastfeeding event data from a removable memory device of the breast support garment 102.

In block 808, the mobile computing device 106 determines whether the system 100 includes a smart pump 108 (i.e., whether a smart pump 108 is used). If so, in block 810, the mobile computing device 106 receives recorded data from the smart pump 108. As described above, the smart pump 108 may record data associated with the breast pumping activities and, in some embodiments, may establish a communication pairing with the breast support garment 102. In block 812, the mobile computing device 106 determines whether the system 100 includes a smart bottle 110 (i.e., whether a smart bottle 110 is used). If so, in block 814, the mobile computing device 106 receives recorded data from the smart bottle 110. As described above, the smart bottle 110 may record data associated with the bottle-feeding activities of the infant. It should be appreciated that, in some embodiments, the data generated by the smart pump 108 and/or the smart bottle 110 may be analyzed, recorded, and/or transmitted to the mobile computing device 106 by the breast support garment 102.

In block 816, the mobile computing device 106 may update the recorded data based on user input. As discussed above, in some embodiments, a user may add, delete, edit, and/or otherwise modify one or more records of the breastfeeding event data. For example, the mother of an infant may add a breastfeeding event that was unrecorded because the mother was wearing a different breast support garment 102 at the time of feeding. In another embodiment, an erroneous breastfeeding event may be removed. In yet another embodiment, a breastfeeding event erroneously identified as a breastfeeding event may be modified to reflect that a breast pump (not an infant) was used.

In block 818, the mobile computing device 106 analyzes the received breastfeeding event data. In doing so, the mobile computing device 106 may determine the breastfeeding routine/pattern of a mother and infant and/or other breastfeeding characteristics. It should be appreciated that such information may be useful, for example, to a pediatrician during a medical examination of the infant. In some embodiments, in block 820, the mobile computing device 106 may coordinate with the cloud computing device 112 for remote analysis of the breastfeeding event data and/or the sensor data itself. In block 822, the mobile computing device 102 may present the results of the analysis to the user. It should be appreciated that those results may be presented in any suitable form depending on the particular embodiment.

EXAMPLES

Illustrative examples of the technologies disclosed herein are provided below. An embodiment of the technologies may include any one or more, and any combination of, the examples described below.

Example 1 includes a smart breast support garment computing system of a breast support garment for monitoring breastfeeding, the smart breast support garment computing system comprising a latch sensor to generate sensor data indicative of a state of a breast latch of the breast support garment; a use sensor to generate sensor data indicative of whether the breast support garment is in use; a context determination module to determine (i) whether the breast support garment is in use based on the sensor data generated by the use sensor and (ii) the state of the breast latch of the breast support garment based on the sensor data generated by the latch sensor; and a recording module to record one or more breastfeeding events in response to a determination that the breast support garment is in use and the breast latch is open.

Example 2 includes the subject matter of Example 1, and wherein to determine whether the breast support garment is in use comprises to determine a state of a latch of the breast support garment.

Example 3 includes the subject matter of any of Examples 1 and 2, and wherein to determine whether the breast support garment is in use comprises to determine whether the breast support garment is in use based on sensor data generated by a temperature sensor positioned on the breast support garment.

Example 4 includes the subject matter of any of Examples 1-3, and wherein to determine whether the breast support garment is in use comprises to determine whether the breast support garment is in use based on sensor data generated by a skin sensor positioned on the breast support garment.

Example 5 includes the subject matter of any of Examples 1-4, and wherein the context determination module comprises a power control module to provide power to components of the smart breast support garment computing system in response to a determination that the breast latch is open.

Example 6 includes the subject matter of any of Examples 1-5, and wherein to record the one or more breastfeeding events comprises to record one or more breastfeeding events that occur between a point in time at which the breast latch is opened and a point in time at which the breast latch is closed.

Example 7 includes the subject matter of any of Examples 1-6, and wherein to record the one or more breastfeeding events comprises to record the one or more breastfeeding events to a removable memory device positioned on the breast support garment.

Example 8 includes the subject matter of any of Examples 1-7, and wherein to record the one or more breastfeeding events comprises to record at least one of a time or duration of breastfeeding.

Example 9 includes the subject matter of any of Examples 1-8, and wherein to record the one or more breastfeeding events comprises to record the one or more breastfeeding events directly to a remote computing device.

Example 10 includes the subject matter of any of Examples 1-9, and further including a communication module to transmit recorded data to a remote computing device for analysis.

Example 11 includes the subject matter of any of Examples 1-10, and wherein the smart breast support garment computing system is attachable to and detachable from a non-smart breast support garment.

Example 12 includes the subject matter of any of Examples 1-11, and wherein the smart breast support garment computing system is physically secured to the breast support garment.

Example 13 includes the subject matter of any of Examples 1-12, and wherein the context determination module is further to determine whether a breast pump is in use; and wherein to record the one or more breastfeeding events comprises to distinguish breastfeeding an infant from the use of the breast pump.

Example 14 includes the subject matter of any of Examples 1-13, and wherein the breast pump is a smart pump; and wherein to determine whether the breast pump is in use comprises to establish a communication pairing with the smart pump.

Example 15 includes the subject matter of any of Examples 1-14, and wherein to determine whether the breast pump is in use comprises to analyze sensed audio data.

Example 16 includes the subject matter of any of Examples 1-15, and wherein the context determination module is further to determine a breast pressure of a wearer of the breast support garment, the breast pressure indicative of an amount of breast milk stored by a corresponding breast of the wearer; and notify a user of the breast support garment in response to a determination that a threshold pressure has been reached.

Example 17 includes a method for monitoring breastfeeding by a smart breast support garment computing system of a breast support garment, the method comprising determining, by the smart breast support garment computing system, whether the breast support garment is in use based on sensor data generated by a use sensor of the smart breast support garment computing system; determining, by the smart breast support garment computing system, a state of a breast latch of the breast support garment based on sensor data generated by a latch sensor of the smart breast support garment computing system; and recording one or more breastfeeding events in response to determining that the breast support garment is in use and the breast latch is open.

Example 18 includes the subject matter of Example 17, and determining whether the breast support garment is in use comprises determining a state of a latch of the breast support garment.

Example 19 includes the subject matter of any of Examples 17 and 18, and wherein determining whether the breast support garment is in use comprises determining whether the breast support garment is in use based on sensor data generated by a temperature sensor positioned on the breast support garment.

Example 20 includes the subject matter of any of Examples 17-19, and wherein determining whether the breast support garment is in use comprises determining whether the breast support garment is in use based on sensor data generated by a skin sensor positioned on the breast support garment.

Example 21 includes the subject matter of any of Examples 17-20, and further including powering components of the smart breast support garment computing system in response to determining that the breast latch is open.

Example 22 includes the subject matter of any of Examples 17-21, and wherein recording the one or more breastfeeding events comprises recording one or more breastfeeding events that occur between a point in time at which the breast latch is opened and a point in time at which the breast latch is closed.

Example 23 includes the subject matter of any of Examples 17-22, and wherein recording the one or more breastfeeding events comprises recording the one or more breastfeeding events to a removable memory device positioned on the breast support garment.

Example 24 includes the subject matter of any of Examples 17-23, and wherein recording the one or more breastfeeding events comprises recording at least one of a time or duration of breastfeeding.

Example 25 includes the subject matter of any of Examples 17-24, and wherein recording the one or more breastfeeding events comprises recording the one or more breastfeeding events directly to a remote computing device.

Example 26 includes the subject matter of any of Examples 17-25, and further including transmitting, by the smart breast support garment computing system, recorded data to a remote computing device for analysis.

Example 27 includes the subject matter of any of Examples 17-26, and further including determining whether a breast pump is in use; wherein recording the one or more breastfeeding events comprises distinguishing breastfeeding an infant from the use of the breast pump.

Example 28 includes the subject matter of any of Examples 17-27, and wherein determining whether the breast pump is in use comprises establishing a communication pairing with the breast pump, the breast pump being a smart pump.

Example 29 includes the subject matter of any of Examples 17-28, and wherein determining whether the breast pump is in use comprises analyzing sensed audio data.

Example 30 includes the subject matter of any of Examples 17-29, and further including determining, by the smart breast support garment computing system, a breast pressure of a wearer of the breast support garment, the breast pressure indicative of an amount of breast milk stored by a corresponding breast of the wearer; and notifying, by the smart breast support garment computing system, a user of the breast support garment in response to determining that a threshold pressure has been reached.

Example 31 includes a computing device comprising a processor; and a memory having stored therein a plurality of instructions that when executed by the processor cause the computing device to perform the method of any of Examples 17-30.

Example 32 includes one or more machine-readable storage media comprising a plurality of instructions stored thereon that, in response to execution by a computing device, cause the computing device to perform the method of any of Examples 17-31.

Example 33 includes a smart breast support garment computing system of a breast support garment for monitoring breastfeeding, the smart breast support garment computing system comprising means for determining whether the breast support garment is in use based on sensor data generated by a use sensor of the smart breast support garment computing system; means for determining a state of a breast latch of the breast support garment based on sensor data generated by a latch sensor of the smart breast support garment computing system; and means for recording one or more breastfeeding events in response to determining that the breast support garment is in use and the breast latch is open.

Example 34 includes the subject matter of Example 33, and the means for determining whether the breast support garment is in use comprises means for determining a state of a latch of the breast support garment.

Example 35 includes the subject matter of any of Examples 33 and 34, and wherein the means for determining whether the breast support garment is in use comprises means for determining whether the breast support garment is in use based on sensor data generated by a temperature sensor positioned on the breast support garment.

Example 36 includes the subject matter of any of Examples 33-35, and wherein the means for determining whether the breast support garment is in use comprises means for determining whether the breast support garment is in use based on sensor data generated by a skin sensor positioned on the breast support garment.

Example 37 includes the subject matter of any of Examples 33-36, and further including means for powering components of the smart breast support garment computing system in response to a determination that the breast latch is open.

Example 38 includes the subject matter of any of Examples 33-37, and wherein the means for recording the one or more breastfeeding events comprises means for recording one or more breastfeeding events that occur between a point in time at which the breast latch is opened and a point in time at which the breast latch is closed.

Example 39 includes the subject matter of any of Examples 33-38, and wherein the means for recording the one or more breastfeeding events comprises means for recording the one or more breastfeeding events to a removable memory device positioned on the breast support garment.

Example 40 includes the subject matter of any of Examples 33-39, and wherein the means for recording the one or more breastfeeding events comprises means for recording at least one of a time or duration of breastfeeding.

Example 41 includes the subject matter of any of Examples 33-40, and wherein the means for recording the one or more breastfeeding events comprises means for recording the one or more breastfeeding events directly to a remote computing device.

Example 42 includes the subject matter of any of Examples 33-41, and further including means for transmitting recorded data to a remote computing device for analysis.

Example 43 includes the subject matter of any of Examples 33-42, and further including means for determining whether a breast pump is in use; wherein the means for recording the one or more breastfeeding events comprises means for distinguishing breastfeeding an infant from the use of the breast pump.

Example 44 includes the subject matter of any of Examples 33-43, and wherein the means for determining whether the breast pump is in use comprises means for establishing a communication pairing with the breast pump, the breast pump being a smart pump.

Example 45 includes the subject matter of any of Examples 33-44, and wherein the means for determining whether the breast pump is in use comprises means for analyzing sensed audio data.

Example 46 includes the subject matter of any of Examples 33-45, and further including means for determining a breast pressure of a wearer of the breast support garment, the breast pressure indicative of an amount of breast milk stored by a corresponding breast of the wearer; and means for notifying a user of the breast support garment in response to determining that a threshold pressure has been reached.

Example 47 includes a mobile computing device for analyzing breastfeeding data of a smart breast support garment, the mobile computing device comprising a data analysis module to (i) receive breastfeeding event data from the smart breast support garment and (ii) analyze the received breastfeeding event data to determine a feeding routine of an infant; and a user interface module to present results of the analysis to a user of the mobile computing device.

Example 48 includes the subject matter of Example 47, and wherein to receive the breastfeeding event data comprises to receive breastfeeding event data from the smart breast support garment based on an established communication pairing with the smart breast support garment.

Example 49 includes the subject matter of any of Examples 47 and 48, and wherein to receive the breastfeeding event data comprises to retrieve event data from a removable memory device of the smart breast support garment.

Example 50 includes the subject matter of any of Examples 47-49, and wherein the data analysis module is further to (i) receive recorded data from a smart breast pump and (ii) analyze the received recorded data from the smart breast pump and the received breastfeeding event data to determine a feeding routine of an infant.

Example 51 includes the subject matter of any of Examples 47-50, and wherein the data analysis module is further to (i) receive recorded data from a smart bottle and (ii) analyze the received recorded data from the smart bottle and the received breastfeeding event data to determine a feeding routine of an infant.

Example 52 includes the subject matter of any of Examples 47-51, and wherein the user interface module is further to update the breastfeeding event data based on input received from a user of the mobile computing device.

Example 53 includes the subject matter of any of Examples 47-52, and further including a communication module to transmit the breastfeeding event data to a cloud computing device for remote analysis.

Example 54 includes a method for analyzing breastfeeding data of a smart breast support garment by a mobile computing device, the method comprising receiving, by the mobile computing device, breastfeeding event data from the smart breast support garment; analyzing, by the mobile computing device, the received breastfeeding event data to determine a feeding routine of an infant; and presenting, by the mobile computing device, results of the analysis to a user of the mobile computing device.

Example 55 includes the subject matter of Example 54, and wherein receiving the breastfeeding event data comprises receiving breastfeeding event data from the smart breast support garment based on an established communication pairing with the smart breast support garment.

Example 56 includes the subject matter of any of Examples 54 and 55, and wherein receiving the breastfeeding event data comprises retrieving event data from a removable memory device of the smart breast support garment.

Example 57 includes the subject matter of any of Examples 54-56, and further including receiving, by the mobile computing device, recorded data from a smart breast pump; and analyzing, by the mobile computing device, the received recorded data from the smart breast pump and the received breastfeeding event data to determine a feeding routine of an infant.

Example 58 includes the subject matter of any of Examples 54-57, and further including receiving, by the mobile computing device, recorded data from a smart bottle; analyzing, by the mobile computing device, the received recorded data from the smart bottle and the received breastfeeding event data to determine a feeding routine of an infant.

Example 59 includes the subject matter of any of Examples 54-58, and further including updating, by the mobile computing device, the breastfeeding event data based on input received from a user of the mobile computing device.

Example 60 includes the subject matter of any of Examples 54-59, and further including transmitting, by the mobile computing device, the breastfeeding event data to a cloud computing device for remote analysis.

Example 61 includes a computing device comprising a processor; and a memory having stored therein a plurality of instructions that when executed by the processor cause the computing device to perform the method of any of Examples 54-60.

Example 62 includes one or more machine-readable storage media comprising a plurality of instructions stored thereon that, in response to execution by a computing device, cause the computing device to perform the method of any of Examples 54-60.

Example 63 includes a mobile computing device for analyzing breastfeeding data of a smart breast support garment, the mobile computing device comprising means for receiving breastfeeding event data from the smart breast support garment; means for analyzing the received breastfeeding event data to determine a feeding routine of an infant; and means for presenting results of the analysis to a user of the mobile computing device.

Example 64 includes the subject matter of Example 63, and wherein the means for receiving the breastfeeding event data comprises means for receiving breastfeeding event data from the smart breast support garment based on an established communication pairing with the smart breast support garment.

Example 65 includes the subject matter of any of Examples 63 and 64, and wherein the means for receiving the breastfeeding event data comprises means for retrieving event data from a removable memory device of the smart breast support garment.

Example 66 includes the subject matter of any of Examples 63-65, and further including means for receiving recorded data from a smart breast pump; and means for analyzing the received recorded data from the smart breast pump and the received breastfeeding event data to determine a feeding routine of an infant.

Example 67 includes the subject matter of any of Examples 63-66, and further including means for receiving recorded data from a smart bottle; means for analyzing the received recorded data from the smart bottle and the received breastfeeding event data to determine a feeding routine of an infant.

Example 68 includes the subject matter of any of Examples 63-67, and further including means for updating the breastfeeding event data based on input received from a user of the mobile computing device.

Example 69 includes the subject matter of any of Examples 63-68, and further including means for transmitting the breastfeeding event data to a cloud computing device for remote analysis.

The invention claimed is:

1. A smart breast support garment computing system of a breast support garment for monitoring breastfeeding, the smart breast support garment computing system comprising:
   a latch sensor to generate sensor data indicative of a state of a breast latch of the breast support garment;
   a use sensor to generate sensor data indicative of whether the breast support garment is in use;
   a context determination module to determine (i) whether the breast support garment is in use based on the sensor data generated by the use sensor and (ii) the state of the breast latch of the breast support garment based on the sensor data generated by the latch sensor; and
   a recording module to record one or more breastfeeding events in response to a determination that the breast support garment is in use and the breast latch is open.

2. The smart breast support garment computing system of claim 1, wherein to determine whether the breast support garment is in use comprises to determine a state of an other latch of the breast support garment.

3. The smart breast support garment computing system of claim 1, wherein to determine whether the breast support garment is in use comprises to determine whether the breast support garment is in use based on sensor data generated by a temperature sensor positioned on the breast support garment.

4. The smart breast support garment computing system of claim 1, wherein to determine whether the breast support garment is in use comprises to determine whether the breast support garment is in use based on sensor data generated by a skin sensor positioned on the breast support garment.

5. The smart breast support garment computing system of claim 1, wherein the context determination module comprises a power control module to provide power to components of the smart breast support garment computing system in response to a determination that the breast latch is open.

6. The smart breast support garment computing system of claim 1, wherein to record the one or more breastfeeding events comprises to record one or more breastfeeding events that occur between a point in time at which the breast latch is opened and a point in time at which the breast latch is closed.

7. The smart breast support garment computing system of claim 1, wherein to record the one or more breastfeeding events comprises to record at least one of a time or duration of breastfeeding.

8. The smart breast support garment computing system of claim 1, wherein to record the one or more breastfeeding events comprises to record the one or more breastfeeding events to a removable memory device positioned on the breast support garment.

9. The smart breast support garment computing system of claim 1, further comprising a communication module to transmit recorded data to a remote computing device for analysis.

10. The smart breast support garment computing system of claim 1, wherein the smart breast support garment computing system is attachable to and detachable from a non-smart breast support garment.

11. The smart breast support garment computing system of claim 1, wherein the smart breast support garment computing system is physically secured to the breast support garment.

12. The smart breast support garment computing system of claim 1, wherein the context determination module is further to determine whether a breast pump is in use; and
   wherein to record the one or more breastfeeding events comprises to distinguish breastfeeding an infant from the use of the breast pump.

13. The smart breast support garment computing system of claim 12, wherein the breast pump is a smart pump; and
   wherein to determine whether the breast pump is in use comprises to establish a communication pairing with the smart pump.

14. The smart breast support garment computing system of claim 12, wherein the use senor generates sensed audio data and to determine whether the breast pump is in use comprises to analyze the sensed audio data.

15. The smart breast support garment computing system of claim 1, wherein the context determination module is further to:
   determine a breast pressure of a wearer of the breast support garment, the breast pressure indicative of an amount of breast milk stored by a corresponding breast of the wearer; and
   notify a user of the breast support garment in response to a determination that a threshold pressure has been reached.

16. One or more non-transitory, machine-readable storage media comprising a plurality of instructions stored thereon that, in response to execution by a smart breast support garment computing system, cause the smart breast support garment computing system to:
   acquire, from a latch sensor of the smart breast support garment computing system, sensor data indicative of a state of a breast latch of a breast support garment;
   acquire, from a use sensor of the smart breast support garment computing system, sensor data indicative of whether the breast support garment is in use;
   determine whether the breast support garment is in use based on the sensor data generated by the use sensor of the smart breast support garment computing system;
   determine a state of the breast latch of the breast support garment based on the sensor data generated by the latch sensor of the smart breast support garment computing system; and
   record one or more breastfeeding events in response to determining that the breast support garment is in use and the breast latch is open.

17. The one or more non-transitory, machine-readable storage media of claim 16, wherein to determine whether the breast support garment is in use comprises to determine a state of an other latch of the breast support garment.

18. The one or more non-transitory, machine-readable storage media of claim 16, wherein to record the one or more breastfeeding events comprises to record one or more breastfeeding events that occur between a point in time at which the breast latch is opened and a point in time at which the breast latch is closed.

19. The one or more non-transitory, machine-readable storage media of claim 16, wherein to record the one or more breastfeeding events comprises to record the one or more breastfeeding events to a removable memory device positioned on the breast support garment.

20. The one or more non-transitory, machine-readable storage media of claim 16, wherein the plurality of instructions further cause the smart breast support garment computing system to power components of the smart breast support garment computing system in response to a determination that the breast latch is open.

* * * * *